United States Patent [19]

Gluzek et al.

[11] 4,396,787

[45] Aug. 2, 1983

[54] PROCESS FOR THE THERMAL DIMERIZATION OF BUTADIENE

[75] Inventors: Karl-Heinz Gluzek, Alpen; Olaf Petersen, Meerbusch; Wilhelm Neier, Rheinberg; Gunter Strehlke, Duisburg; Karl-Heinz Heinemann, Neukirchen-Vluyn, all of Fed. Rep. of Germany

[73] Assignee: Deutsche Texaco Aktiengesellschaft, Fed. Rep. of Germany

[21] Appl. No.: 324,331

[22] Filed: Nov. 23, 1981

[30] Foreign Application Priority Data

Dec. 1, 1980 [DE] Fed. Rep. of Germany ....... 3045229

[51] Int. Cl.$^3$ ............................................. C07C 3/035
[52] U.S. Cl. ..................................... 585/366; 585/510
[58] Field of Search ............... 585/365, 366, 360, 361, 585/317, 318; 208/44 R; 422/231, 901

[56] References Cited

U.S. PATENT DOCUMENTS 3,674,679 7/1972 Washimi et al. ................... 208/48 R
4,144,307 3/1979 Cohen ................................. 422/901

FOREIGN PATENT DOCUMENTS 2237865 2/1975 France ................................. 585/366
1138126 12/1968 United Kingdom ................ 585/366

OTHER PUBLICATIONS

Windholz, Editor, The Marck Index, (1976) p. 1117.

Primary Examiner—Delbert E. Gantz
Assistant Examiner—A. Pal
Attorney, Agent, or Firm—Carl G. Ries; Robert A. Kulason; Carl G. Seutter

[57] ABSTRACT

Formation of undesirable popcorn polymer on the walls of a reaction vessel during thermal dimerization of butadiene is prevented by coating the walls with a falling film of aqueous sodium nitrite solution.

9 Claims, 1 Drawing Figure

U.S. Patent  Aug. 2, 1983  4,396,787
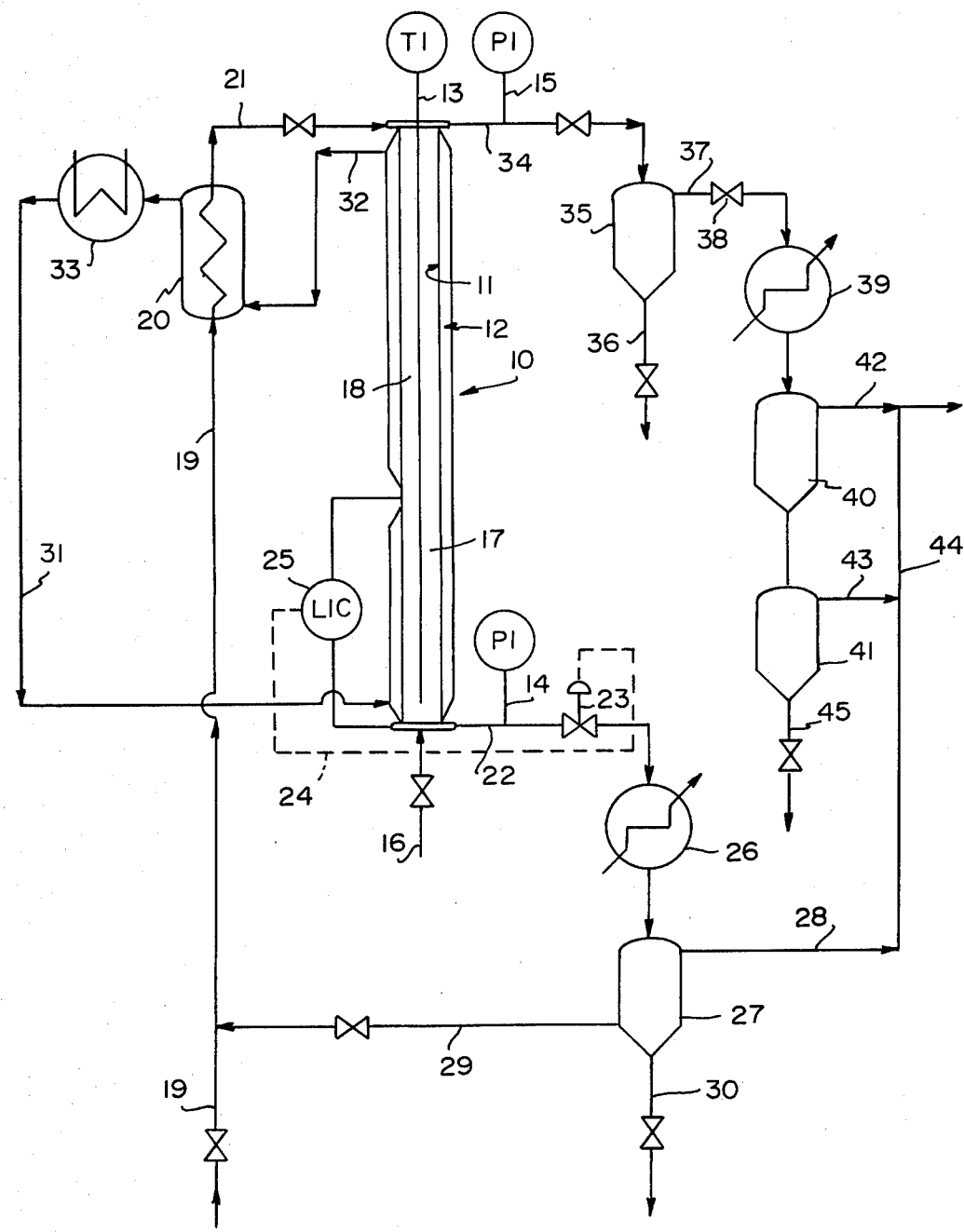

PROCESS FOR THE THERMAL DIMERIZATION OF BUTADIENE

FIELD OF THE INVENTION

This invention relates to a process for the thermal dimerization of butadiene.

BACKGROUND OF THE INVENTION

Processes for the thermal dimerization of conjugated diolefins are known. However, particularly in the thermal dimerization of butadiene, undesired high-molecular weight polymers are formed which are termed "popcorn" polymers due to their shape. So-called "germs" are formed which act as starting points for further polymerization. These "germs" primarily settle on the walls of the reactors and grow towards the interior of the apparatus, blocking the passageways and building up pressure drop across the apparatus.

Since the "popcorn" polymerizate is insoluble in common solvents it is impossible to wash it out. Owing to the strong adhesion and the partially tacky consistency, the mechanical removal is difficult, and it is impossible to remove it from the piping of commercial plants. Even if the apparatus were purged with utmost care, small particles remain which favor subsequent growth of undesired polymer. The "popcorn" polymerization thus causes loss of valuable raw material and noticeably increases the total production cost as a result of plugging of reaction apparatus and piping.

To avoid this undesired polymerization it has been suggested to use an organic solvent as reaction medium. In U.S. Pat. No. 2,411,822, for instance, kerosine is recommended as a solvent. In U.S. Pat. No. 3,454,665, a paraffinic washing oil with a boiling point of approx. 215° C. is recommended. However, the amount of soluble polymerizate formed in this process is considerable, though "popcorn" polymerizate is not mentioned in these patent specifications.

According to Industrial and Engineering Chem., Vol. 39, No. 7, pages 830-837, gaseous nitrogen dioxide and aqueous sodium nitrite solutions are employed as general polymerization inhibitors. This publication made in 1947 refers to the prevention of styrene and butadiene polymerization in storage tanks and facilities connected in series with the styrene synthesis reactor. The aqueous solution of sodium nitrite is particularly referred to as an inhibitor for styrene polymerization and as an inorganic antioxidant. Its efficiency was tested in both cases at 55° C. and it was found that (basis the inhibition effect at this temperature) styrene remained liquid for 100 to 200 days. At a temperature of 100° C., which is a very high one for such facilities, styrene remained liquid for only 14 days. The use of aqueous sodium nitrite solution in polymerization processes as such for preventing formation of "popcorn" during polymerization is not taught in this publication. This understandable, because the polymerization processes as such, particularly the thermal polymerization processes are performed at noticeably higher temperatures.

For preventing "popcorn" polymerization in the thermal dimerization of conjugated olefins a great variety of inhibitors has been suggested. In U.S. Pat. No. 2,943,117 an aromatic solvent, e.g. benzene in combination with an aqueous solution of a diamine or with aqueous ammonia solution of a diamine or with aqueous ammonia solution is recommended. However, using this process the formation of high-molecular polymers cannot be completely prevented.

In the German Auslegeschriften Nos. 20 38 311 and 21 15 858 the use of N-substituted N-nitrosohydroxylamines is suggested. However, these systems are expensive and can only be used at temperatures of up to 140° C.

According to DE-OS 18 16 826 dating from 1968, the susceptibility of butadiene to polymerize in solutions is lowered by adding aromatic nitro-compounds as polymerization inhibitors. On page 2, lower paragraph of said publication it is literally stated that at room temperature or lower temperatures the polymerization of butadiene can be prevented to a certain extent by adding conventional, known polymerization inhibitors, e.g. hydroquinone, 4-tert. butyl catechol, betanaphthyl amine, methylene blue, sodium nitrite etc.:

"However, the aforementioned polymerization inhibitors are not satisfactorily efficent with respect to preventing polymerization of butadiene, if the butadiene-containing solution is exposed to relatively high temperatures, e.g. 80° C. to 160° C. or even higher for an extended period of time."

Hence, it may be understood from said Offenlegungsschrift that sodium nitrite is unsuitable for inhibiting "popcorn" formation at the temperatures stated therein.

STATEMENT OF THE INVENTION

In accordance with certain of its aspects, the process of this invention for thermal dimerization of butadiene in an upstanding reaction vessel comprises:

passing an aqueous alkali metal nitrite solution to the head of said upstanding reaction vessel;

passing a film of said solution from the head downwardly over the internal surfaces of said upstanding reaction vessel;

withdrawing said solution from a lower portion of said upstanding reaction vessel;

passing to said upstanding reaction vessel a charge gas stream containing butadiene;

maintaining a temperature of about 180° C.–260° C. and a pressure of about 50–250 bar in said upstanding reaction vessel whereby said butadiene is thermally dimerized to form product stream containing vinyl cyclohexene; and recovering said product stream containing vinyl cyclohexene.

DESCRIPTION OF THE INVENTION

According to the present invention, it was surprisingly found that aqueous alkali nitrite solution is capable of inhibiting the formation of "popcorn" even at higher temperatures without impairing the desired dimerization. This is effected by coating the walls and surfaces of the reaction vessel and other pieces of apparatus with aqueous alkali nitrite solution, because only in this way the inhibitor is fully efficient.

When the reaction vessel is a column, as in one preferred embodiment, it is preferred to coat the inside of the column with a continuous film of aqueous sodium nitrite solution. This may be effected by spraying the solution into the top of the column so that the solution forms a continuous downwardly moving, falling film on the walls of the column. Spraying is preferably carried out to provide aqueous solution in the vapor phase, too.

It is advantageous to charge the starting material to be dimerized and the alkali nitrile solution in countercurrent operation to the reactor, the alkali nitrite solution being fed to the reactor head.

The charge stream which may be admitted to the process of this invention may be a refinery hydrocarbon gas stream containing butadiene. Although it is possible to utilize a stream of pure butadiene, it is more common to use a technical-grade C$_4$-pyrolysis cut containing typically about 35 w.% butadiene.

It is known that technical-grade C$_4$-pyrolysis cuts or C$_4$-hydrocarbon mixtures may contain small amounts of oxygen due to leakage and insufficient nitrogen purging of apparatus or containers for storage and transportation, due to disturbances in the stage for producing C$_4$-cuts, due to oxygen initiation in the production of polybutadiene or butadiene-styrene copolymerizates. The oxygen content in such C$_4$-cuts may be between 0.001% up to 1.0 w.% or more and is thus a disturbing factor which has to be eliminated.

It is preferred that, prior to use, the charge hydrocarbon stream containing butadiene be treated with hydrogen in the presence of hydrogenation catalyst typified by platinum or palladium on alumina or silica carrier. Hydrogenation will minimize the content of oxygen and peroxo compounds. It is also preferred that the charge hydrocarbon stream containing butadiene be freshly distilled prior to use. For economic reasons, sodium nitrite is preferred as alkali nitrite, but other nitrites, for instance potassium nitrite are also suitable. The alkali-metal nitrite concentration in the aqueous solution may typically be between 4 and 40% wt.; an approx. 7% aqueous sodium nitrite solution is preferred. Commonly used inhibitors contained in the starting material to improve the storage stability of the diolefin do not interfere at the high temperatures to be employed. Therefore, they need not be removed from the feed gas. It is particularly surprising that an aqueous alkali nitrite solution can be used in the thermal dimerization to prevent formation of "popcorn", because among others DE-OS No. 18 16 826 teaches that sodium nitrite is unsuitable as an inhibitor for "popcorn" formation at the temperatures employed, see the tables of examples 2, 4, 5, and 7 of said publication, line 2 each. Similar statements are also made in U.S. Pat. No. 3,407,240.

In the practice of the process of this invention, thermal dimerization of butadiene may be carried out in vapor phase in a reaction vessel in which the surfaces with which the contents contact are coated with a film of aqueous alkali metal nitrite in the solution. It is also preferred that the solution be present as a spray in the vapor spaces.

As thermal dimerization of the butadiene occurs typically at 180° C.–260° C. and 50–250 Bar in the presence of the apparatus walls which are coated with the film of aqueous alkali metal nitrite solution, it is found that the walls and surfaces which have been coated with this film are free of undesirable popcorn polymer; and the dimerization reaction proceeds satisfactorily.

DESCRIPTION OF THE DRAWING

The charge to the process of this invention to be carried out in the attached drawing may be first hydrogenated (not shown). This may be effected by passing charge hydrocarbon upwardly in liquid phase together with hydrogen through a vertical tubular reactor containing platinum-on-alumina hydrogenation catalyst. Operation is at 10 bar pressure. Hydrogenation will remove residual oxygen and peroxy compounds.

In practice of the process of this invention in certain of its aspects, the aqueous alkali metal nitrite may be admitted to the head of a column or to the upper portion of the vessel, as by means of a spray head or a conduit in manner to substantially coat the interior of the reactor with a thin film of nitrite solution. This thin falling film protects the surfaces of the reaction vessel from being coated with popcorn polymer. The aqueous alkali metal nitrite solution may be collected in a lower position of the apparatus and withdrawn.

For the dimerization reaction, high temperatures are advantageous. Usually temperatures of 180° C.–260° C., particularly 200° C.–240° C. may be used. The yield drops at lower temperatures. When C$_4$-pyrolysis cut is used as feed gas, a temperature of about 230° C.–250° C. is preferred.

A higher pressure favors the desired cyclization reaction. The maximum pressure is determined by the constructional features of the reaction apparatus. Pressures of 50–250 bar may be employed. Good conversions are attained at pressures of above about 100 bar. A pressure of 150 bar may be preferred.

Practice of the thermal dimerization process proper according to a preferred embodiment of the invention may be carried out in a countercurrent tower or reactor assembly 10 as shown in the drawing. The reactor assembly 10 includes a vertically positioned column 11 surrounded by a jacket 12 through which heat exchange fluid is passed for heating or cooling as desired. The column 11 is fitted with a thermocouple 13 for measuring the temperature at selected elevations of the column, and with pressure meters 14 and 15 adjacent to the bottom and to the top to measure the pressure at these points and the pressure drop therebetween during operation.

In operation charge feed gas (e.g. a technical grade C$_4$ pyrolysis cut containing butadiene) is admitted through line 16 to the lower end of the column. It bubbles upwardly through the collected body of aqueous sodium nitrite solution at 17 and thence upwardly through the vapor space 18 of column 11.

As the upwardly ascending charge hydrocarbon feed stream containing butadiene passes through the vapor space 18 in column 11, the butadiene is dimerized in vapor phase to form product stream containing vinyl cyclohexene. Reaction occurs at about 230° C.–250° C. and 150 bars pressure.

In this embodiment, there is admitted a 6 w.%–7 w.% inhibitor aqueous sodium nitrite solution through line 19. It passes through heat exchanger 20 and line 21 through which it is admitted by means of a spray to the upper end of column 11. The spray deposits inhibiting liquid on the internal surfaces of column 11 and in particular forms a continuous downwardly descending film on the inside surface of the column 11. The downwardly descending film is collected in liquid body 17 in column 11.

Aqueous sodium nitrite solution is withdrawn from body 17 through line 22 and control valve 23 which, through circuit 24 and level controller 25, maintains liquid in body 17 in column 11 at a predetermined level. After passing through heat exchanger 26, the liquid is collected in vessel 27. Vapor therefrom may be removed through line 28 and liquid through line 29. Liquid in line 29 may be adjusted to proper concentration as by addition of water (to replace that volatilized in vessel 10) and recycled if desired to line 19. Lines 30 and 19 provide for withdrawal and admission of nitrite solution.

Vessel 10 may be maintained at desired temperature by heat exchanger jacket 12 through which heating oil passes. Hot oil is admitted through line 31 and cool oil is withdrawn through line 32. Cool oil, which is still quite hot, may be exchanged against charge liquid in line 19 to preheat the latter in heat exchanger 20. Inhibitor solution in line 19 may be heated to desired temperature in heat exchanger 20.

Stream 34 leaving the reactor overhead contains residual unreacted gas, dimerizate product, and evaporated water. It also contains ammonia generated by reduction of a portion of the nitrite. The stream in line 34 is passed to high pressure separator 35. Ammonia and water are withdrawn through line 36.

Uncondensed organic phase is removed through line 37 and depressurized through valve 38 to atmospheric pressure. This is then condensed in heat exchanger 39 and recovered in vessels 40 and 41. Uncondensed gases are withdrawn through lines 42, 43 and 44 and desired product dimerizate in liquid phase is recovered through line 45.

DESCRIPTION OF PREFERRED EMBODIMENTS

Practice of the process of this invention will be apparent to those skilled in the art from the following examples which illustrate the present invention.

EXAMPLE 1

The dimerization reactor was an upright tube reactor with an inside diameter of 2.6 cm and an overall length of 150 cm. The nitrite was removed 50 cm above the reactor bottom. The temperature was measured with a displaceable thermocouple located in a centrally placed thermometer cartridge with a diameter of 0.6 cm. The reaction tube was jacketed and indirectly heated with Texatherm ® heat exchange oil. The reactor was flooded up to the level-controlling valve with an approx. one-molar sodium nitrite solution (6.9% wt. sodium nitrite).

To the reactor bottom, 140 grams of C₄-pyrolysis cut, low loaded (approx. 71 Nl/h), with a butadiene content of 35% wt. were fed per hour. At the same time 0.5 liter of 6.9% sodium nitrite solution (1 liter/liter.h) was charged to the reactor head. The same amount of nitrite was continuously removed via the level-controlling valve. For the total nitrite recycle, 10 liters of inhibitor solution were used. The temperature in the reactor was 200° C.; the reaction pressure was 150 bar.

Reaction product, evaporated water, and residual gas was removed overhead from the reactor. In the high-pressure water separator 35 approx. 4 grams of water were separated per hour. After single-stage pressure release, the organic products were collected in the gas-liquid separator 40 and stabilized by heating to boiling (ca 125° C.).

24 grams of stabilized dimerizate and 116 grams of residual gas were obtained per hour. The residual gas contained on an average 1% wt. vinylcyclohexene.

| Composition of the Stabilized Crude Dimerizate | |
|---|---|
| Gas | 0.2% wt. |
| Divinylcyclobutane | 1.4% wt. |
| Vinylcyclohexene | 84.8% wt. |
| Cyclooctadiene-1,5 | 7.2% wt. |

| -continued | |
|---|---|
| Composition of the Stabilized Crude Dimerizate | |
| Unknowns | 4.8% wt. |
| Soluble Oligomers | 1.6% wt. |
| | (b.p. 100° C./14 Torr) |

Hence the total conversion of butadiene per pass was 51% wt.

Every 250 operating hours the inhibitor volume was supplemented with 1 liter of fresh nitrite solution. After 1,500 operating hours the reactor was opened. No solid polymerizate (popcorn) was found therein.

EXAMPLE 2

The reactor was charged, as described in example 1, with 160 grams of pure butadiene and 0.5 liter of 6.9% sodium nitrate solution. The temperature was 200° C. and the total pressure was 150 bar. 118 grams of stabilized dimerizate, 42 grams of residual gas, and 5 grams of water were obtained per hour.

The dimerizate contained 0.1% butadiene, 1.6% divinylcyclobutene, 86.7% vinylcyclohexene, 6.5% cyclooctadiene, 3.9% trimers, and 1.2% soluble oligomers.

The butadiene conversion was 73.8% per pass.

After 350 operating hours no polymers were found.

EXAMPLE 3

The reactor was charged, as described in example 1, with 150 grams of C₄-pyrolysis cut (butadiene content 49.3% wt., acetylene content less than 0.2% wt.) and 0.5 liter of 6.9% sodium nitrite solution. The temperature was 240° C., the pressure was 150 bar. 66.1 grams of dimerizate, 83.9 grams of residual gas, and 4 grams of water were obtained per hour. The dimerizate contained 0.1% gas, 0.2% divinylcyclobutene, 81.7% vinylcyclohexene, 3.6% trimers, and 6.0% unknowns.

The butadiene conversion was 89.4% pass.

After 240 operating hours the reactor was opened. No polymerizate was found.

EXAMPLE 4

The reactor was charged, as described in example 1, with 150 grams of C₄-pyrolysis cut having a butadiene content of 48.8% wt. and an acetylene content of 0.9% wt. To the reactor head 0.5 liter of 6.9% sodium nitrite solution was charged. The temperature was 240° C., the pressure was 190 bar. 67.4 grams of dimerizate, 82.6 grams of residual gas, and 4 grams of water were obtained per hour. The dimerizate contained 0.4% gas, 80.4% vinylcyclohexene, 4.2% ethylcyclohexene, 0.5% vinylcyclohexadiene, 8.2% cyclooctadiene, 3.7% trimers, and 2.6% oligomers.

The butadiene conversion was 91.2% per pass.

EXAMPLE 5

Unlike example 1, both 0.5 liter of 6.9% sodium nitrite solution (1 liter/liter.h) and 150 grams of C₄-pyrolysis cut (approx. 76 Nl/h) with a butadiene content of 49.5% wt. were fed to the reactor head. After cooling and separating the organic phase, the inorganic phase was collected in the gas-liquid separator 7 after single-stage pressure release and was stabilized. Apart from that, the tube reactor was operated as described in example 1.

59.8 grams of dimerizate and 90.2 grams of residual gas were obtained. The dimerizate contained 0.2% wt.

gas 0.9% divinylcyclobutene, 81.5% vinylcyclohexene, 2.2% ethylcyclohexene, 0.8% vinylcyclohexadiene, 7.3% cyclooctadiene, 3.2% trimers, and 3.9% unknowns.

The reactor was opened after 400 operating hours. No polymerizate (popcorn) was found. The butadiene conversion was 80.5% per pass.

EXAMPLE 6

In this example the charge was first hydrogenated to remove oxygen by passing through a pre-reactor which was packed with a palladium catalyst on $Al_2O_3$; hydrogen was used as inert gas. The reactor, as described in example 1, with 150 grams of $C_4$-pyrolysis cut (approx. 76 Nl/h) with a butadiene content of 35% wt. At the same time 0.5 liter of 6.9% sodium nitrite solution (1 liter/liter.h) was fed to the reactor head. The temperature in the reactor was 240° C., the reaction pressure was 190 bar. 33.6 grams of dimerizate and 116.4 grams of residual gas were obtained per hour. The dimerizate contained 0.1% gas, 0.8% divinylcyclobutene, 80.4% vinylcyclohexene, 2.8% ethylcyclohexene, 0.5% vinylcyclohexadiene, 8.2% cyclooctadiene, 5.3% unknowns, and 1.9% oligomers. The butadiene conversion was 64% per pass. Every 250 operating hours the inhibitor volume was supplemented with one liter of fresh nitrite solution. The reactor was opened after 1,500 operating hours. No solid polymerizate (popcorn) was found therein.

COMPARISON EXAMPLE 1

The experiment described in example 1 was repeated, the difference being that desalted water instead of the inhibitor solution was fed to the reactor. The charge and temperature and pressure conditions were equal to those of example 1. After four hours the experiment had to be discontinued, because the charged water left the reactor overhead and a pressure difference of more than 10 bar had been built up. After opening the reactor approx. 50 grams of polymerizate were found on the walls of the reactor.

The dimerizate composition was equal to that shown in example 1.

COMPARISON EXAMPLE 2

The reactor described in example 1 was charged with 250 ml of a 6.9% sodium nitrite solution and heated to 200° C. To the bottom of the reactor 140 grams of $C_4$-pyrolysis cut with 35% wt. butadiene were fed per hour and removed overhead together with the formed dimerizate so that the overall pressure was 150 bar. At the reactor head only the water obtained in the water separator was recycled. Product yield and gas composition were equal to those of example 1. After 8 hours a pressure difference of 15 bar had been built up. When inspecting the open reactor approx. 35 grams of polymerizate were found on the walls of the reactor above the nitrite level.

Comparison example 2 shows that mere presence of nitrite is not sufficient for efficient inhibition. It is essential that the alkali nitrite solution be charged to the head of the reactor and that it be present as a falling film on the reactor walls.

The process for the thermal dimerization of conjugated diolefins serves both for isolating the diolefin from hydrocarbons mixtures by decomposing the dimerizate produced and for preparing the dimerizate as a chemical intermediate. Thus the vinylcyclohexene prepared by dimerization of butadiene serves for the preparation of styrene via ethyl benzene.

Although this invention has been illustrated by reference to specific embodiments, it will be apparent to those skilled in the art that various changes and modifications may be made which clearly fall within the scope of the invention.

We claim:
1. The process for thermal dimerization of butadiene in an upstanding reaction vessel which comprises;
    passing an aqueous alkali metal nitrite solution to the head of said upstanding reaction vessel;
    passing a film of said solution from the head downwardly over the internal surfaces of said upstanding reaction vessel;
    withdrawing said solution from a lower portion of said upstanding reaction vessel;
    passing to said upstanding reaction vessel a charge gas stream containing butadiene;
    maintaining a temperature of about 180° C.–260° C. and a pressure of about 50–250 bar in said upstanding reaction vessel whereby said butadiene is thermally dimerized to form product stream containing vinyl cyclohexene; and
    recovering said product stream containing vinyl cyclohexene.
2. The process for thermal dimerization of butadiene as claimed in claim 1 wherein said charge gas stream containing butadiene is freshly distilled prior to admission to said reaction vessel.
3. The process for thermal dimerization of butadiene as claimed in claim 1 wherein said charge gas stream containing butadiene is hydrogenated in the presence of hydrogenation catalyst, thereby removing oxygen and peroxo compounds from said charge gas stream prior to admission to said reaction vessel.
4. The process for thermal dimerization of butadiene as claimed in claim 1 wherein said dimerization is carried out in an upright tubular reactor.
5. The process for thermal dimerization of butadiene as claimed in claim 1 wherein said charge gas stream containing butadiene passed upwardly through said reactor countercurrent to the flow of downwardly descending aqueous alkali metal nitrite solution.
6. The process for thermal dimerization of butadiene as claimed in claim 1 wherein said aqueous alkali metal nitrite solution is a 4 w%–40 w% solution.
7. The process for thermal dimerization of butadiene as claimed in claim 1 wherein said aqueous alkali metal nitrite solution is a 4 w%–9 w% solution.
8. The process for thermal dimerization of butadiene as claimed in claim 1 wherein said aqueous alkali metal nitrite solution is sodium nitrite solution.
9. The process for thermal dimerization of butadiene in an upstanding tubular reactor which comprises:
    passing a 4 w%–9 w% aqueous sodium nitrite solution to the head of said upstanding tubular reaction vessel;
    passing a film of said solution downwardly over the internal surface of the tubes of said upstanding tubular reaction vessel;
    withdrawing said solution from a lower portion of said upstanding reaction vessel;
    passing to a lower portion of said upstanding tubular reactor a charge gas stream containing butadiene;
    passing said charge gas stream upwardly countercurrently with respect to said downwardly descending aqueous sodium nitrite solution;

maintaining a temperature of about 180° C.–260° C. and a pressure of about 50–250 bar in said upstanding tubular reaction vessel, whereby said butadiene is thermally dimerized to form product stream containing vinyl cyclohexene; and recovering said product stream containing vinyl cyclohexene from the overhead of said upstanding tubular reaction vessel.

* * * * *